United States Patent
Baruch

(10) Patent No.: US 11,229,371 B2
(45) Date of Patent: Jan. 25, 2022

(54) BUTTERFLY CUFF

(71) Applicant: CareTaker Medical, LLC, Charlottesville, VA (US)

(72) Inventor: Martin Baruch, Charlottesville, VA (US)

(73) Assignee: CareTaker Medical, LLC, Charlottesville, VA (US)

( * ) Notice: Subject to any disclaimer, the term of this patent is extended or adjusted under 35 U.S.C. 154(b) by 218 days.

(21) Appl. No.: 16/209,707

(22) Filed: Dec. 4, 2018

(65) Prior Publication Data
US 2019/0167128 A1 Jun. 6, 2019

Related U.S. Application Data

(60) Provisional application No. 62/594,299, filed on Dec. 4, 2017.

(51) Int. Cl.
*A61B 5/022* (2006.01)
*A61B 5/024* (2006.01)
(Continued)

(52) U.S. Cl.
CPC ...... *A61B 5/02241* (2013.01); *A61B 5/02444* (2013.01); *A61B 5/14542* (2013.01);
(Continued)

(58) Field of Classification Search
CPC . A61B 5/02241; A61B 5/02444; A61B 5/022; A61B 5/02233; A61B 5/6825; A61B 5/6826; A61B 5/6829; A61B 5/6831
See application file for complete search history.

(56) References Cited

U.S. PATENT DOCUMENTS 4,846,189 A 6/1989 Sun
6,491,647 B1 12/2002 Bridger et al.
(Continued)

FOREIGN PATENT DOCUMENTS

CN 1771005 A 5/2006
CN 106344042 A 1/2017
(Continued)

OTHER PUBLICATIONS

Advancing Safety in Medical Technology; Non-invasive sphygmomanometers—Part 2: Clinical investigation of automated measurement type; ANSI/AAMI/ISO 81060-2:2013.
(Continued)

*Primary Examiner* — Eric J Messersmith

(57) ABSTRACT

A cuff for monitoring physiological cycles has an exterior and interior surface and securing means. The cuff consists of a body having an upper curve, a lower curve and a height (CH) therebetween. A sensor adhered with a flexible protective overlay to the interior surface is in communication with a microprocessor storage means. The microprocessor storage means can be within the cuff or separate therefrom with communication between the sensor and the storage means being wireless or through a communication member. A locking tab, having a width less than the body, extends from one side of the body. A slot retaining area extends from the body on a side opposite the locking tab and contains a slot dimensioned to receive the locking tab. A pull tab is adjacent the slot retaining area opposite the body. The pull tab shares a base with the slot retaining area and has a top line and an end width less than the width of the body. The cuff can be manufactured from a hook and loop material or have other securing methods to affix the cuff in place.

21 Claims, 5 Drawing Sheets

(51) Int. Cl.
*A61B 5/145* (2006.01)
*G16H 40/67* (2018.01)
*G16H 40/63* (2018.01)

(52) U.S. Cl.
CPC ........ *A61B 2562/164* (2013.01); *G16H 40/63* (2018.01); *G16H 40/67* (2018.01)

(56) References Cited

U.S. PATENT DOCUMENTS

| | | | |
|---|---|---|---|
| 6,723,054 | B1 | 4/2004 | Baruch |
| 7,087,025 | B2 | 8/2006 | Baruch |
| 8,100,835 | B2 | 1/2012 | Baruch |
| 2002/0116797 | A1* | 8/2002 | Modgil ............. A61B 5/14552 24/306 |
| 2006/0253041 | A1 | 11/2006 | Shin et al. |
| 2007/0287923 | A1 | 12/2007 | Adkins et al. |
| 2008/0046054 | A1 | 2/2008 | Hjelle et al. |
| 2009/0318779 | A1 | 12/2009 | Bao |
| 2010/0056886 | A1 | 3/2010 | Hurtubise et al. |
| 2010/0222655 | A1 | 9/2010 | Starr et al. |
| 2010/0262022 | A1 | 10/2010 | Baruch et al. |
| 2010/0317945 | A1* | 12/2010 | Schraa ............... A61B 5/02241 600/324 |
| 2012/0238887 | A1* | 9/2012 | Gerdt ................. A61B 5/02116 600/499 |
| 2012/0330109 | A1 | 12/2012 | Bao |
| 2014/0066792 | A1* | 3/2014 | Lin .................... A61B 5/02233 600/492 |
| 2015/0148694 | A1 | 5/2015 | Baruch |
| 2015/0186609 | A1 | 7/2015 | Utter, II |
| 2016/0045119 | A1 | 2/2016 | Gerdt et al. |
| 2016/0120420 | A1 | 5/2016 | Liedl |
| 2019/0029542 | A1* | 1/2019 | Li ....................... A61B 5/6826 |
| 2019/0059825 | A1 | 2/2019 | Baruch |
| 2019/0104953 | A1* | 4/2019 | Narasimhan ......... A61B 5/7235 |

FOREIGN PATENT DOCUMENTS

| | | |
|---|---|---|
| EP | 0 264 848 B1 | 2/1993 |
| EP | 2 471 444 A1 | 7/2012 |

OTHER PUBLICATIONS

Babbs, CF: Oscillometric Measurement of Systotic and Diastolic Blood Pressures Validated in a Physiological Mathematical Model: Biomed Engineering Online; Aug. 22, 2012; 11:56; https://doi.org/10.1186/1475-925X-11-56.

Gizdulich, P; Prentza, A; Wesseling, KH: Models of Brachial to Finger Pulse Wave Distortion and Pressure Decrement; Cardiovascular Research; Mar. 1997; 33(3);698-705.

International Search Report and Written Opinion dated Oct. 25, 2018, for International Application No. PCT/US2018/041093, 8 pages.

International Search Report and Written Opinion dated Apr. 18, 2019, for International Application No. PCT/US2018/063890, 8 pages.

Lee, JY; Kim, JK; Yoon, G; Digital Envelope Detector for Blood Pressure Measurement Using an Oscillometric Method; Journal Medical Engineering & Technology; May-Jun. 2002 (3); 117-22.

Lyew, MA; Jamieson, JW; Blood Pressure Measurement Using Oscillometric Finger Cuffs in Children and Young Adults. A Comparison with Arm Cuffs During General Anesthesia; Anesthesia; Oct. 1994; 49(10): 895-9.

Nesselroad, JM: Flacco, VA; Phillips, DM; Kruse, J; Accuracy of Automated Finger Blood Pressure Devices, Family Medicine Mar. 1996; p. 28(3):189-92.

Veerman DP; Lenders, JW; Thein T; Van Montfrans, GA; LAM 100/Marshall F-88: Accuracy and Precision of a New Device for Discontinuous Finger Blood Pressure Measurement; Journal of Human Hypertension, Apr. 1993; 7(2):113-5.

Extended European Search Report dated Apr. 8, 2021, for European Application No. 18828614.0, 13 pages.

Extended European Search Report dated Jul. 28, 2021, for European Application No. 18886394.8, 9 pages.

* cited by examiner

BUTTERFLY CUFF

CROSS-REFERENCE TO RELATED APPLICATIONS

This application claims priority to and the benefit of U.S. Provisional Application No. 62/594,299, filed Dec. 4, 2017, the disclosure of which is hereby incorporated by reference herein in its entirety.

FIELD OF THE INVENTION

The present invention relates generally to a noninvasive cuff for continuous or non-continuous monitoring of blood pressure (cNIBP) in arteries without occluding blood flow in the finger. In the case of oscillometric calibration, the cuff is used as an agent to gradually occlude the artery in order to arrive at an absolute blood pressure calibration.

BACKGROUND OF INVENTION

Finger cuffs are an excellent non-invasive method of monitoring blood pressure, heart rate, respiration rate, blood volume changes, and many other hemodynamic parameters; however, the core issues of using finger cuffs to hydraulically, or pneumatically, couple to the digital arteries remain unresolved. In order to obtain consistent, reliable readings with cuffs on fingers or other extremities, the placement of the cuff, the tension in the cuff, the rigidity of the enclosure formed by the cuff, and the ease of use of the cuff are all critically important.

Reliable and repeatable placement on the finger is critical to obtain consistent and reliable readings. This is particularly the case because there are two digital arteries in each finger, an issue that brachial blood pressure cuffs do not have to contend with. If the cuff is placed asymmetrically, increasing pressure will cause the bladder to engage initially one and then the other artery, thus distorting the oscillometric curve obtained during the pressure scan and making a reliable calibrated blood pressure determination difficult or impossible.

Reliable and repeatable tension in the finger cuff is likewise critical. To achieve this, conformity to the conical, oblong shape of the finger joint is critical.

Rigidity of the enclosure formed by the finger cuff is critical because the bladder, or sensing area, pressure has to be directed uniformly toward the digital arteries. When the enclosure contains the pressurizable bladder it must be inextensible in tension yet very flexible when wrapped around, for instance, a finger. If the enclosure stretches, especially dynamically., the bladder pressure will drop, distorting the true arterial pressure envelope.

In order to obtain consistent readings, it should also be intuitively obvious to a clinician how to apply the cuff to a patient's finger and how to tighten the cuff in a repeatable manner.

Current solutions for obtaining accurate readings involve flexible or rigid solutions that come in different sizes to accommodate finger sizes. One attempt to resolve the above issues has been the use of buckles. Buckles have, however, proven to be non-workable because the reversal of the enclosure end tab that is required to cinch the enclosure around the finger disrupts the conformity of the enclosure. This problem worsens as finger diameter decreases. Buckles are also not optimal because the reversal of the single enclosure end easily de-centers the enclosure on the arteries, making it necessary to rotate the enclosure, and the bladder within it, back into the correct position. Buckles also require more manipulation of the technician's fingers with further demands on manual dexterity than does a butterfly cuff.

SUMMARY OF THE INVENTION

A cuff for monitoring physiological cycles has an exterior and interior surface and securing means. The cuff consists of a body having an upper curve, a lower curve and a height CH therebetween. A sensor is adhered to the interior surface with a flexible protective overlay, and the sensor is in communication with a microprocessor storage means. The microprocessor storage means can be within the cuff or separate therefrom with communication between the sensor and the storage means being wireless or through a communication member. A locking tab, having a width less than the body, extends from one side of the body. A slot retaining area extends from the body on a side opposite the locking tab and contains a slot dimensioned to receive the locking tab. A pull tab is adjacent the slot retaining area opposite the body. The pull tab shares a base with the slot retaining area and has a top line and an end width less than the width of the body. The cuff can be manufactured from a hook and loop material or have other securing methods to affix the cuff in place.

In use the sensor is placed adjacent a user's artery, and the locking tab threaded through the slot. The pull tab and locking tab are pulled in opposite directions until tight and secured in position.

In an optimally dimensioned example, the body has an upper curve with a radius of about 2.126 inches, a lower curve with a radius of about 0.919 inch, a height of about 1.976 inches and a length of about 6.728 inches. The locking tab extends from the body at an angle of about 12° from the base of the cuff and has a height of about 0.875 inches. The slot within the slot retaining area is at an angle of about 80° from the base of the cuff. The top line of the pull tab is at about a 27° angle from the base of the cuff.

In use the sensor contained in the interior of the cuff body adjacent a user's artery; the locking tab threaded through the slot within the slot retaining area. Pressure is then applied to the locking tab and the pull tab, in opposite directions, to tighten the cuff. The ends of the locking tab and the pull tab are then secured to the cuff.

BRIEF DESCRIPTION OF THE DRAWINGS

These and other objects, features, advantages and aspects of the present invention can be better understood with reference to the following detailed description of the preferred embodiments when read in conjunction with the appended drawing figures.

DETAILED DESCRIPTION OF THE INVENTION

Definitions

Figure 1:
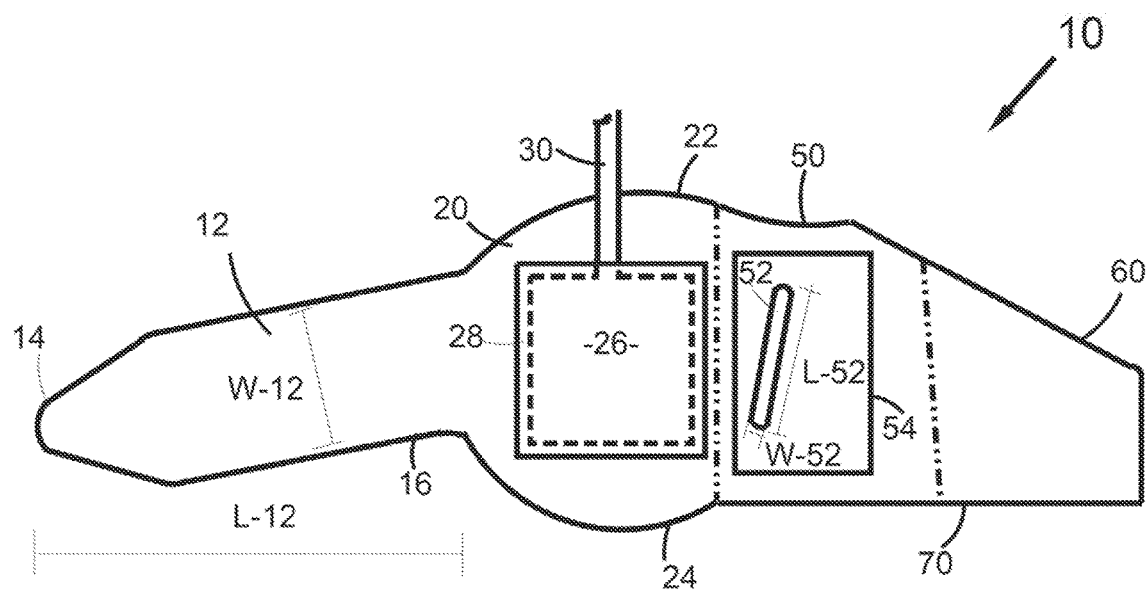
FIG. 1 is a plan view of the interior side of the cuff in accordance with the invention.

As used herein the term "sensor" shall refer to any type of sensing device that can detect events or changes in a physical property and records, indicates, or otherwise responds to the events and/or changes, including but not limited to a pressure sensor and oximeter. Information is generally transmitted from the sensor to a microprocessor storage device either through a physical connection or wirelessly. Generally sensors convert a physical quantity to an electrical signal.

As used herein the term "transducer" is a device that converts variations in a physical quantity, such as brightness or pressure, into an electrical signal or vice versa. Generally, transducers can work in reverse, that is they work both ways.

As used herein the term "coupler" is something that connects two things, especially mechanical components or as systems such as a hydraulic coupler. The butterfly cuff is a coupler and not a sensor or a transducer.

For the purposes herein the term "about" shall refer to plus or minus ten percent (10%) although the preferred variation is dependent upon maintaining the criteria as set forth herein.

The present invention relates to a wireless and noninvasive physiological monitoring system in the form of a hydrostatic cuff for measuring heart rate variability (HRV), blood pressure, hypovolemia, hypervolemia, inter-beat interval, abnormal patterns, arrhythmia, and other physiological cycles. Additionally, the monitoring system in the case of absolute blood pressure measurement, may force changes over a time period such as forcing a ten mmHg rise every four seconds until a maximum desirable pressure is achieved. In addition to pressure derived data, an oximeter source and detector may be embedded into the cuff which would provide a measurement of blood oxygenation or SpO2. Monitored data can be stored within the device for later download using a connection to a PDA or PC, via a connection such as USB, Bluetooth, etc. Alternatively the data can be sent to the receiving device in real time.

The solution to the foregoing problems is provided by a slotted, butterfly-like design having a shape as disclosed. The curved design naturally conforms to a conical shape thus yielding a fitted, tapered enclosure, as opposed to forming a cylindrical enclosure that stands off at one end due to the tapering of a finger, leg, foot or arm.

In adults the cuff 10 would be placed around a finger and positioned to make contact with the digital arteries. The disclosed cuff can also be placed on the arms and legs of infants, specifically premature infants, who need careful monitoring of heart rate during the first three minutes of life. The disclosed cuff allows for checking of heart beat rate within seconds of birth.

In contrast to current methods, using the disclosed cuff provides heart rate determination that is almost instantaneous and recovers almost immediately after motion induced noise stops. Although the drawings and reference hereinafter are directed at the use of the cuff on fingers, it can also be used on other appendages, as noted above, on legs and arms, such as those of small children or infants.

Figure 2:
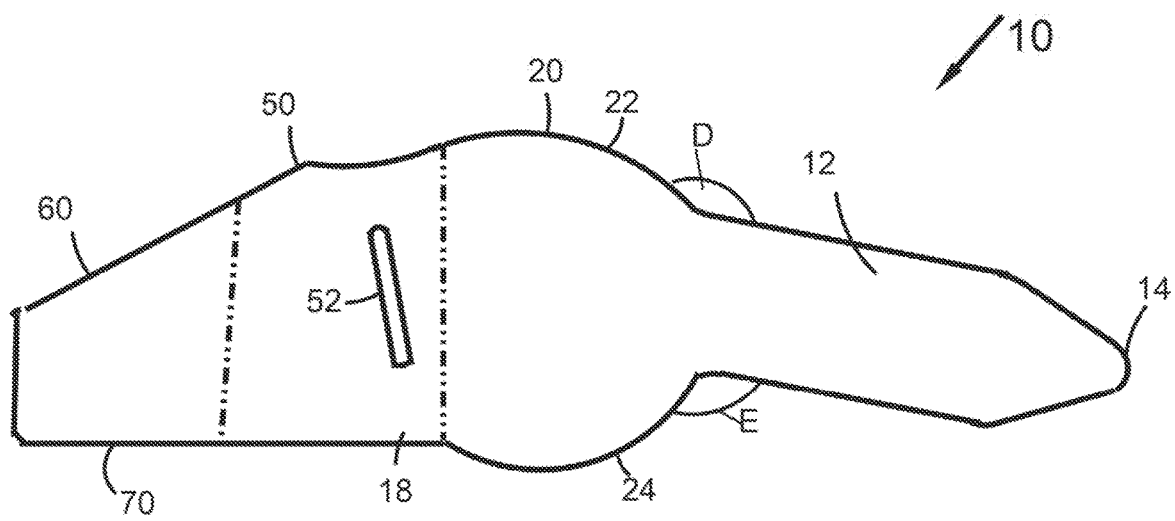
FIG. 2 is a plan view of the exterior side of the cuff in accordance with the invention.

As illustrated in FIGS. 1 and 2, the cuff 10 comprises a locking tab 12, a curved body 20, receiving slot area 50 and pull tab 60. All reference to upper and lower as used herein is for description purposes only and unless noted otherwise, are interchangeable. The phantom lines illustrated in these figures are for clarity of description and to identify locations within the cuff; they are not included within the actual cuff. For ease of manufacture and cost, the cuff, in most applications, will be manufactured from hook and loop material, however other materials and methods of adhesion can be used. For example, a flexible material as used in adhesive bandages can be used with the locking tab 12 and pull tab 60 having a protective strip over the adhesive portion. This construction does, however, have the disadvantage for long term use in that the cuff cannot be readjusted. If a plastic strip is preferable, the hook and loop fastener strips as used on disposable diapers can be used. Alternatively, a flexible, non-stretch material can be used and the locking tab secured with an appropriate securing member.

Figure 3:
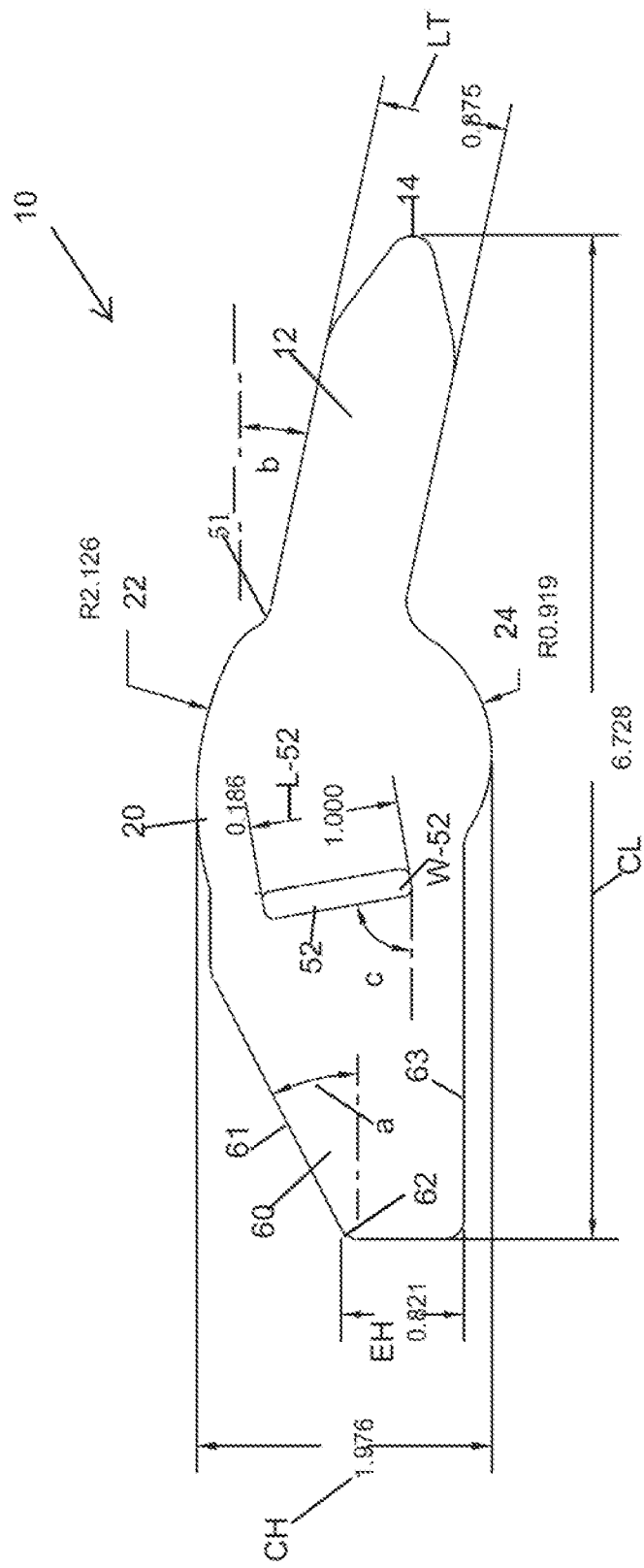
FIG. 3 is a plan view of the exterior side of the cuff with example dimensions in accordance with the invention.

The length L-12 and width W-12 of the locking tab 12 are dependent upon the size of the extremity, such as finger, infant leg or arm, etc., with the criteria being that the locking tab 12 must extend a sufficient distance around the extremity to securely hold the sensing area 26 in contact with the digital arteries. An example including optimal dimensions is illustrated in FIG. 3. The locking tab 12 is an elongated strip with a tapered end 14 to facilitate insertion into the angled slot 52. The length L-12 is, as an example, in the range of about one (1) to about two (2) inches and a width W-12 in the range of about one half (0.5) to about one (1) inch. These measures can be varied by +/−25% or more, depending on the extremity to which the cuff is being applied, and will be obvious to those skilled in the art.

A single sized cuff 10 will accommodate a range of finger sizes, however the elements should be sized appropriately for effective results. When the sensing area 26 is placed on the digital arteries, the curved body 20 must be sufficiently close to the width of the user's extremity to enable locking tab 12 to pass through the angled slot 52 and tighten. Thus, the body 20 cannot come in contact with the angled slot 52 as contact would prevent the proper pressure from being applied.

The curved body 20 is formed by upper curve 22 and lower curve 24. As illustrated, the upper curve 22 has less of a curvature than the lower curve 24. The gentler upper curve 22 is placed at a position on the extremity proximal to the user's body, while lower curve 24 is positioned on the extremity distal to the user's body. For example, when the cuff is placed on a finger, upper curve 22 is placed at a position on the finger closest to the hand while the lower curve 24 is placed at a position on the finger closest to the tip of the finger. The upper curve 22 and lower curve 24 can change with the sizing of the cuff 10; however, it is critical that they maintain uniform backing of the pressure-containing sensing area 26 against the digital arteries subject to the conical taper of the finger and its oblong cross section.

The locking tab 12 extends from the curved body 20 at an angle to maintain, when closed, the curvature of the finger. There are two angles between the locking tab 12 and the body 20 forming a concave lower angle E and convex upper angle D as illustrated in FIG. 2.

The slot retaining area 50 is positioned between the body 20 and the pull tab 60, opposite that of the locking tab 12, and contains the angled tab slot 52. The tab slot 52 is angled in order to maintain the sensing area 26 in the proper position against the arteries when the cuff 10 is secured with the angle of the slot 52 being dependent on the angle of the locking tab 12. The preferred angles of both slot 52 and locking tab 12 are relative to pull tab base 63. The length L-52 of the tab slot 52 is slightly greater than the width W-12 of the locking tab 12 and the width W-52 slightly greater than the thickness of the material of manufacture. The slot retaining area 50 has a slight curve 51 to provide comfort to the user at the area of the finger joint. The curve should not extend into the overlay 54 to avoid weakening the structural integrity of the overlay 54.

The interior 16 of the cuff 10, which would be placed against the user's skin and as illustrated in FIG. 1, contains the sensor 26 and communication member 30, which provides communication between the sensor 26, for example a piezo-electric element and a microprocessor or other storage or readout device. The method of communication will be dependent upon the type of sensor 26 and its capabilities and will be known to those skilled in the art. For example, if the sensing area 26 is part of a bladder, the communication will be pneumatic, or if the sensor 26 is a sensor, such as a piezo-electric element, the communication will be electric via wireless (FIG. 6) or wired means. It should be noted that the cuff in FIG. 6 has the same structure as that of FIGS. 1-5 with the only change depicting a wireless. The sensor 26 is protected and secured to the curved body 20 by an overlay 28. The overlay 28 is a highly flexible material that is biocompatible and will not interfere with the working of the sensor 26 or the wrapping of the cuff 10 around the user's finger. In some applications, due to the type of sensor, the overlay 28 can be eliminated. The overlay 28 must be able to be securely adhered to the material used for manufacture of the cuff 10, for example glue, fusing, stitching, etc.

The slot overlay 54 is adhered to the slot retaining area 50 prior to the slot 52 being cut. The slot overlay 54 prevents any tearing or widening of the slot 52, thereby keeping constant pressure on the arteries. The slot overlay 54 also greatly facilitates clinical workflow usage of the cuff by reducing the possibility of premature engagement of hook and loop when locking tab 12 is inserted into angled slot 52, particularly at a low angle. Preventing premature engagement is therefore critical for readily obtaining a snug fit of the cuff 10 around the finger.

The pull tab 60 is a solid portion of the cuff 10 used to tighten, in conjunction with the locking tab 12, the cuff 10 as described hereinafter. In this design the baseline 70 extends, on the same plane, between the pull tab 60 and the slot retaining area 50, however the dimensions can vary based on manufacture.

To facilitate proper placement on the appendage, desired coupling and pressure to the arteries, and communication with the sensor, the dimensions of the cuff 10 are critical. FIG. 3 illustrates an example of the optimal angles and dimensions. Based on the illustrated cuff length CL of about 6.728 inches optimum results will be achieved when angles are only varied by one degree and dimensions by 1/32 inch. To substantially increase or decrease the cuff length, the dimensions and radii must be adjusted proportionally.

An example of optimal dimensions is illustrated in FIG. 3 and can be used to increase or decrease the cuff 10 size. The cuff 10 having an overall cuff length CL of about 6.728 inches has a locking tab 12 width LT of about 0.875 inch and a cuff height CH of about 1.976 inches. The pull tab 60 has an end height of about 0.821 inch to provide for sufficient gripping area. The slot 52 preferably has rounded ends with a length L-52 of about 1.0 inch and slot width W-52 of about 0.186 inch. The upper curve 22 has a radius of about 2.126 inches while the lower curve 24 has a radius of about 0.919 inch. To obtain the appropriate pressure on the artery, fit and ease of application, the angles within the cuff 10 are critical. Angle "A" is about 27° and represents the angle between the top line 61 of the pull tab 60 and the pull tab base 63. Angle "B" is about 12° and represents the angle between the locking tab 12 and the pull tab base 63. Angle "C" is about 80° and represents the angle of the slot 52 to the pull tab base 63.

Figure 4:
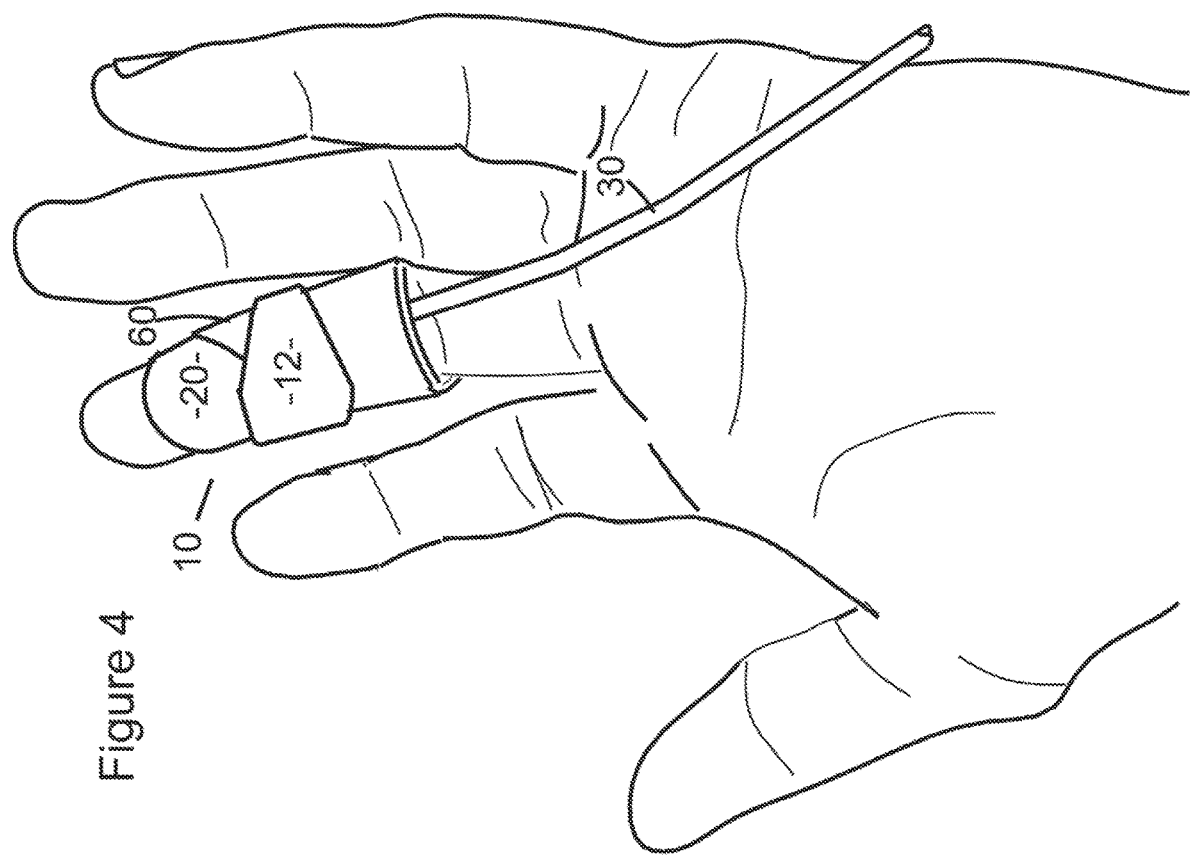
FIG. 4 is a front view of the finger cuff wrapped around a person's finger in accordance with the invention.
Figure 5:
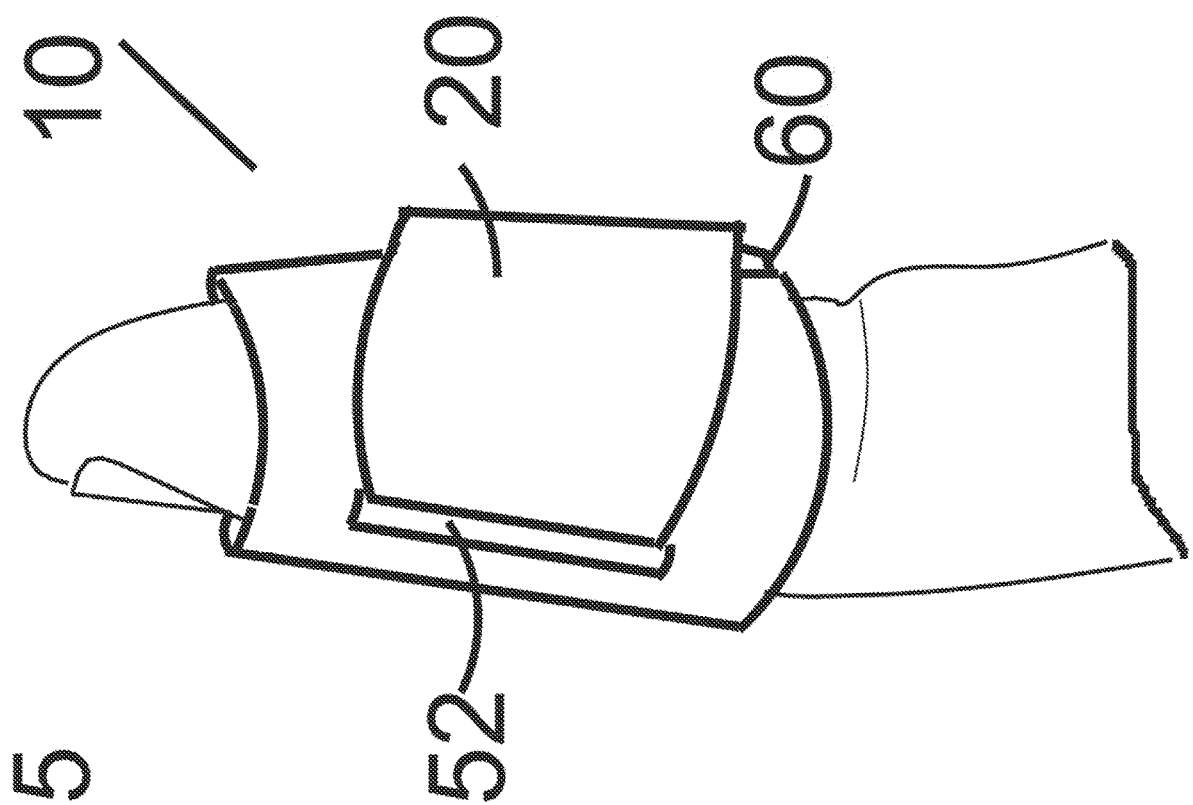
FIG. 5 is a side view of the finger cuff wrapped around a person's finger in accordance with the invention.
Figure 6:
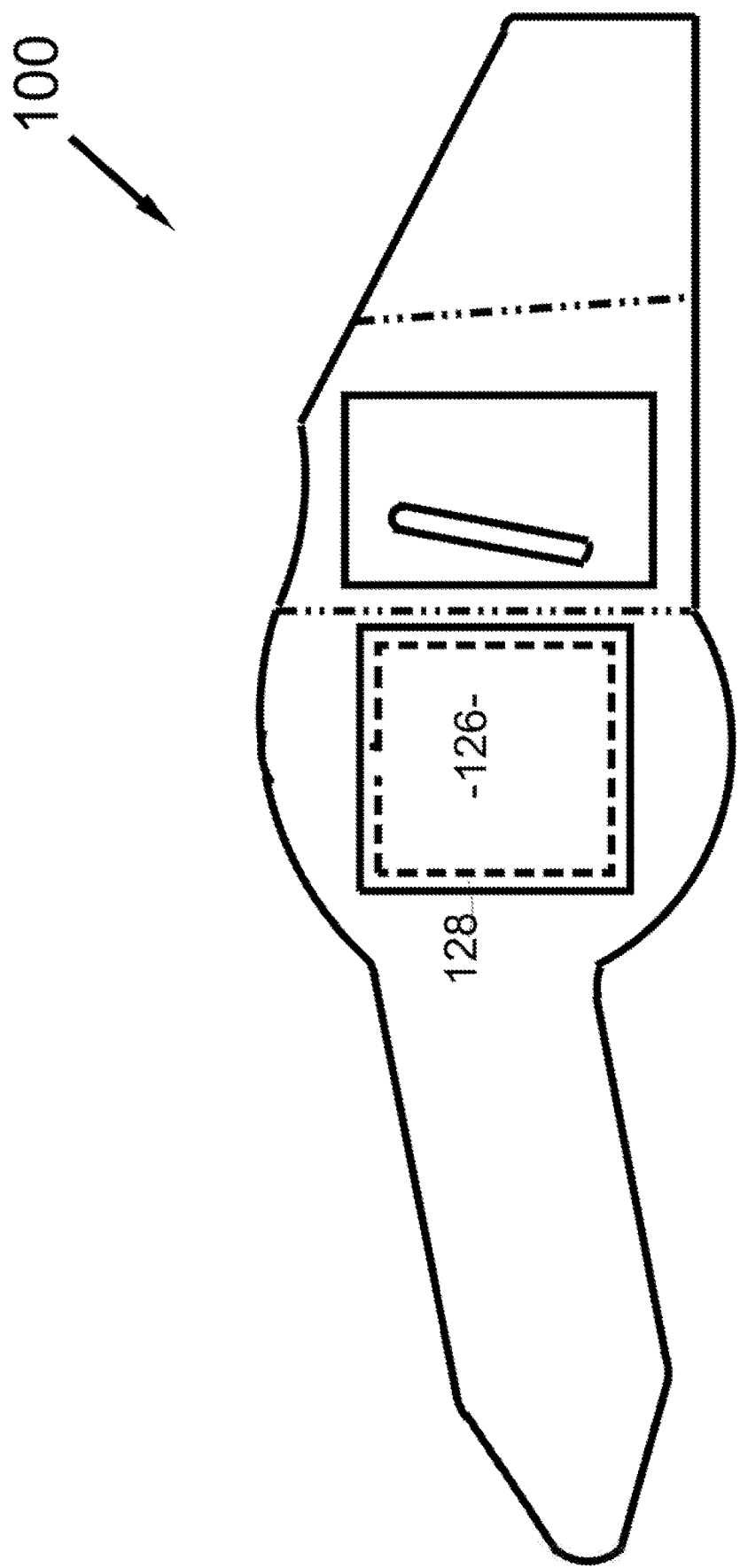
FIG. 6 is a plan view of the interior of the cuff with a sensor having wireless communication in accordance with the invention.

FIGS. 4 and 5 show the cuff 10 wrapped around a user's finger. As can be seen the curved body 20 is positioned over the digital artery with the tube 30 extending therefrom. Pull tab 60 has been secured to the curved body 20 and the locking tab 12 secured over the pull tab 60. FIG. 5 shows the locking tab 20 pulled through the slot 52 and adhered over the pull tab 60.

To use the cuff 10 the sensing area 26 is positioned over the arteries and the locking tab 12 is passed through the slot 52. Upon passing the locking tab 12 through the slot 52, two opposing tabs are created, locking tab 12 and pull tab 60, that will pull in opposite directions. The positioning of the locking tab 12 and pull tab 60 makes it intuitively obvious for a clinician to evenly tighten the cuff 10 around the extremity. The even pressure facilitates keeping the sensing area 26 centered on the arteries. The pull tab 60 is then secured followed by the locking tab 12, securing the cuff 10 in position.

Similarly, upon passing the locking tab 12 through the slot 52, the opposing locking tab 12 and pull tab 60, make it possible to continuously adjust the circumference of the cuff 10 enclosure around the finger.

The disclosed cuff can be readily operated by a single user with little training. Placing the cuff 10, for example, on the left middle finger, the locking tab 12, upon insertion through the slot 52 can be held between index finger and thumb, while the other hand pulls on the opposing, pull tab 60 and engages it with the fastening mechanism, such as hook and loop material, beneath. Once the pull tab 60 is secured the locking tab 12 is secured on top of the pull tab 60, and the cuff 10 is ready for use The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Multiple embodiments are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about", "substantially", or "approximately." Similarly, the numerical values in the various ranges specified in this application, unless expressly indicated otherwise, are stated as approximations as though the minimum and maximum values within the stated ranges were both preceded by the word "about", "substantially", or "approximately." In this manner, variations above and below the stated ranges can be used to achieve substantially the same results as values within the ranges. As used herein, the terms "about", "substantially", and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about", "substantially", or "approximately" will serve to broaden a particular numerical value or range. Thus, as a general matter, "about", "substantially", or "approximately" broaden the numerical value. Also, the disclosure of ranges is intended as a continuous range including every value between the minimum and maximum values plus the broadening of the range afforded by the use of the term "about", "substantially", or "approximately". Thus, recitation of ranges of values herein are merely intended to serve as a shorthand method of referring individually to each separate value falling within the range, unless otherwise indicated herein, and each separate value is incorporated into the specification as if it were individually recited herein. To the extent that determining a given amount of variation of some the factors such as the criticality of the slit patterns, paper width differential pre- and post-expansion, paper weights and type, as well as other considerations known to those of skill in the art to which the disclosed subject matter is most closely related or the art relevant to the range or element at issue will have on the performance of the claimed subject matter, is not considered to be within the ability of one of ordinary skill in the art, or is not explicitly stated in the claims, then the terms "about", "substantially", and "approximately" should be understood to mean the numerical value, plus or minus 10%.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A cuff for monitoring physiological cycles, comprising:
    a body having an upper curved edge, a lower curved edge, an exterior surface, and an interior surface;
    a sensor adhered to said interior surface and in communication with a microprocessor storage device;
    a locking tab extending from said body and having a width from a first edge of the locking tab to an opposing second edge of the locking tab less than a maximum width between said upper curved edge and said lower curved edge of said body;
    a slot retaining portion extending from an opposite side of said body than said locking tab and defining a slot configured to receive said locking tab; and
    a pull tab extending from said slot retaining portion in a direction away from said body, the pull tab having an upper edge and a lower edge, a minimal width between said upper edge and said lower edge of the pull tab being less than said maximum width between said upper curved edge and said lower curved edge of said body,
    wherein said sensor is configured to be placed adjacent a user's artery, said locking tab is configured to be placed into said slot, and said pull tab and said locking tab are each configured to be pulled in opposite directions to secure said body relative to said user's artery.

2. The cuff of claim 1, wherein said locking tab extends from a centerline of said body at a non-zero angle.

3. The cuff of claim 2, wherein said non-zero angle is about 12°.

4. The cuff of claim 1, wherein said locking tab has a width from said first edge of said locking tab to said second edge of said locking tab of about 0.875 inches.

5. The cuff of claim 1, wherein said upper edge of said pull tab is disposed at about a 27° angle from said lower edge of said pull tab.

6. The cuff of claim 1, wherein said lower curved edge has a radius of about 0.919 inches.

7. The cuff of claim 1, wherein said upper curved edge has a radius of about 2.126 inches.

8. The cuff of claim 1, wherein said slot is disposed at a non-zero and non-perpendicular angle relative to said lower edge of said slot retaining portion.

9. The cuff of claim 8, wherein said angle is about 80°.

10. The cuff of claim 1, wherein said communication is wireless.

11. The cuff of claim 1, wherein said communication is wired.

12. The cuff of claim 1, further comprising a flexible overlay configured to protect said sensor and secured to said interior surface of said body.

13. The cuff of claim 1, wherein said cuff has an overall length of about 6.728 inches and said maximum width of said body is about 1.976 inches.

14. The cuff of claim 1, wherein said microprocessor storage device is disposed within said cuff.

15. The cuff of claim 1, wherein said cuff includes a hook and loop material such that said locking tab and said pull tab can be secured relative to each other via the hook and loop material.

16. The cuff of claim 1, further comprising an adhesive portion disposed on an interior surface of said cuff such that said locking tab and said pull tab can be secured relative to each other via the adhesive portion.

17. A cuff for monitoring physiological cycles, comprising:
    a body having an upper curved edge having a radius of about 2.126 inches, a lower curved edge having a radius of about 0.919 inches, a maximum width of about 1.976 inches and an overall length of about 6.728 inches;
    a sensor adhered to said interior surface and in communication with a microprocessor storage device;
    an overlay protecting said sensor;
    a locking tab having a width from a first edge of the locking tab to an opposing second edge of the locking tab of about 0.875 inches;

a slot retaining portion extending from an opposite side of said body than said locking tab and defining a slot; and
a pull tab extending from said slot retaining portion in a direction away from said body, the pull tab having an upper edge and a lower edge, a minimal width between said upper edge and said lower edge of the pull tab being less than said maximum width of said body,
wherein said locking tab extends from a centerline of said body at an angle of about 12°,
wherein said slot is disposed within said slot retaining portion at an angle of about 80° relative to a lower edge of said slot retaining portion,
wherein said upper edge of said pull tab is disposed about a 27° angle from said lower edge of said pull tab, and
wherein said sensor is configured to be placed adjacent a user's artery, said locking tab is configured to be placed into said slot, and said pull tab and said locking tab are configured to be pulled in opposite directions to a desired tightness, and said locking tab and said pull tab are configured to be secured relative to each other.

18. The cuff of claim 17, wherein said communication is wireless.

19. The cuff of claim 17, wherein said communication is wired.

20. A method of noninvasively monitoring at least one hemodynamic parameter comprising the steps of:
  a. placing a sensor having a communication member contained in the interior of a cuff body adjacent a user's artery;
  b. threading a locking tab extending from said cuff body through a slot within a slot retaining portion;
  c. applying pressure in opposite directions to said locking tab and a pull tab to tighten a cuff, said pull tab disposed opposite said slot retaining portion from said cuff body; and
  d. adhering said locking tab and said pull tab to said cuff body,
  wherein data transmitted from said communication member indicates said at least one hemodynamic parameter arterial blood pressure.

21. The method of claim 20, wherein the at least one hemodynamic parameter includes at least one of heart rate variability, blood pressure, hypovolemia, hypervolemia, inter-beat interval, or arrhythmia.

* * * * *

UNITED STATES PATENT AND TRADEMARK OFFICE
CERTIFICATE OF CORRECTION

| | |
|---|---|
| PATENT NO. | : 11,229,371 B2 |
| APPLICATION NO. | : 16/209707 |
| DATED | : January 25, 2022 |
| INVENTOR(S) | : Martin Baruch |

It is certified that error appears in the above-identified patent and that said Letters Patent is hereby corrected as shown below:

In the Claims

At Column 9, Lines 13-14 (Claim 17, Lines 26-27): "is disposed about a 27° angle" should read --is disposed at about a 27° angle--

At Column 10, Lines 17-18 (Claim 20, Lines 15-16): "hemodynamic parameter arterial blood pressure." should read --hemodynamic parameter.--

Signed and Sealed this
Thirteenth Day of June, 2023

Katherine Kelly Vidal
*Director of the United States Patent and Trademark Office*